(12) United States Patent
Cicchitti

(10) Patent No.: US 7,424,780 B2
(45) Date of Patent: Sep. 16, 2008

(54) DEVICE FOR CUTTING SANITARY CONTAINERS, IN PARTICULAR SACKS, BAGS, AND/OR POUCHES FOR STOMAS

(75) Inventor: Marco Cicchitti, Atessa (IT)

(73) Assignee: Easystem S.r.L., Lanciano (CH) (IT)

( * ) Notice: Subject to any disclaimer, the term of this patent is extended or adjusted under 35 U.S.C. 154(b) by 42 days.

(21) Appl. No.: 10/575,630

(22) PCT Filed: Apr. 30, 2004

(86) PCT No.: PCT/IT2004/000239

§ 371 (c)(1),
(2), (4) Date: Apr. 13, 2006

(87) PCT Pub. No.: WO2005/034821

PCT Pub. Date: Apr. 21, 2005

(65) Prior Publication Data

US 2007/0056417 A1  Mar. 15, 2007

(30) Foreign Application Priority Data

Oct. 14, 2003  (IT) .......................... RM2003A0471

(51) Int. Cl.
*B43L 9/04* (2006.01)

(52) U.S. Cl. ...................... 33/27.03; 33/27.031; 30/310

(58) Field of Classification Search ................. 33/27.03, 33/27.031; 30/310, 316, 360
See application file for complete search history.

(56) References Cited

U.S. PATENT DOCUMENTS

| | | | |
|---|---|---|---|
| 4,753,010 A | 6/1988 | Franovich | |
| 4,924,574 A | 5/1990 | Jones et al. | |
| 5,361,664 A | 11/1994 | Desmarais | |
| 6,131,498 A | 10/2000 | Gerber | |
| 6,286,216 B1 * | 9/2001 | Braun | 33/27.031 |

FOREIGN PATENT DOCUMENTS

GB  2239832 A  *  7/1991

* cited by examiner

*Primary Examiner*—Yaritza Guadalupe-McCall
(74) *Attorney, Agent, or Firm*—Young & Thompson

(57) ABSTRACT

A device for cutting sanitary containers, in particular sacks, bags, and/or pouches for stomas, includes a structure (2) provided with a housing portion (3). The housing portion (2) has a cutting plate (4, 10) whereon is set down a container to be cut. The cut is accomplished by cutting elements (23) associated with the structure (2). The cutting elements (13) are adapted to cut a structural portion of the container, defining its inlet. The cutting elements are further provided with adjusting elements (17) to determine the amplitude and the shape of the inlet of the container being prepared, in relation to the shape and the dimensions of the stoma of a patient.

17 Claims, 5 Drawing Sheets

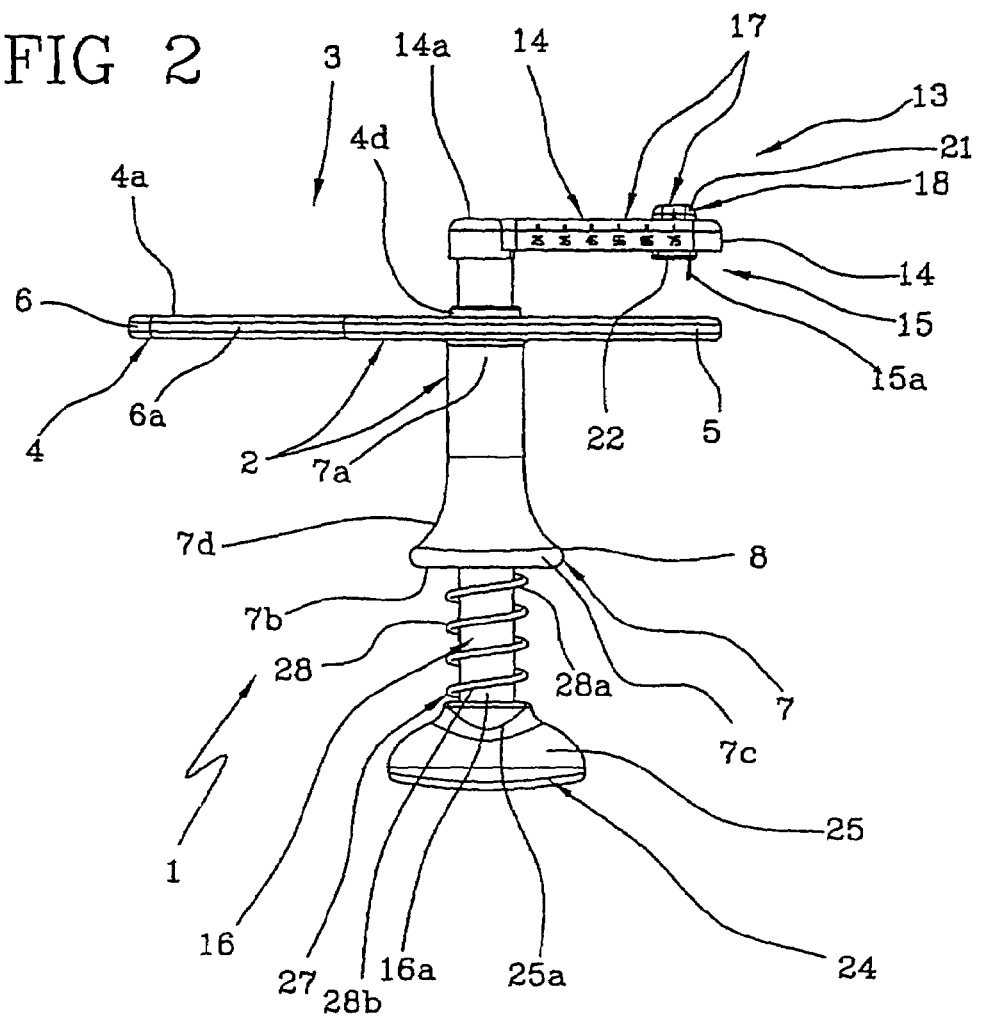
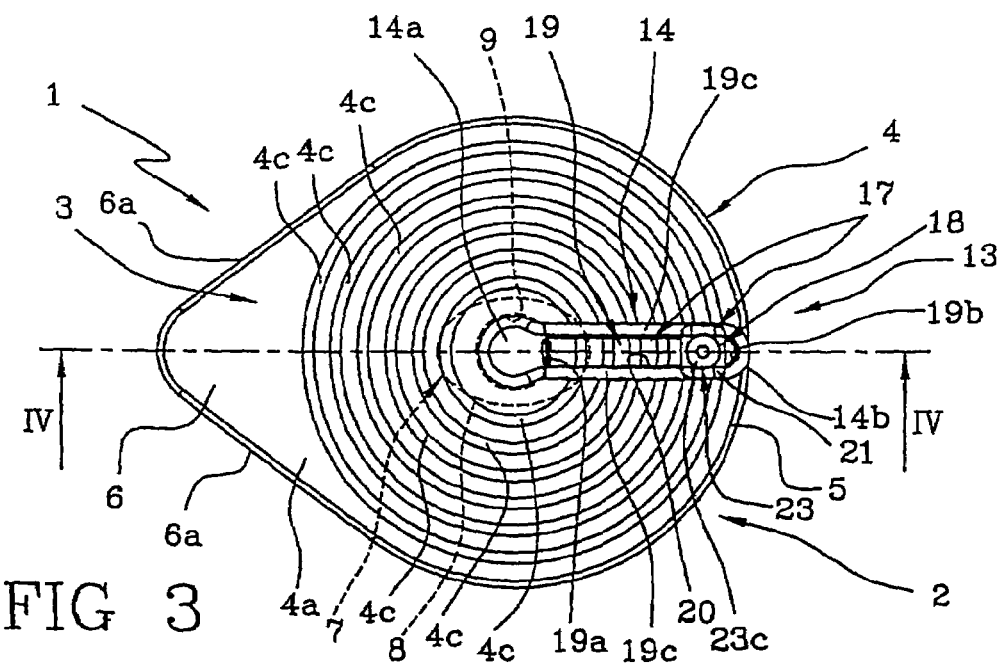

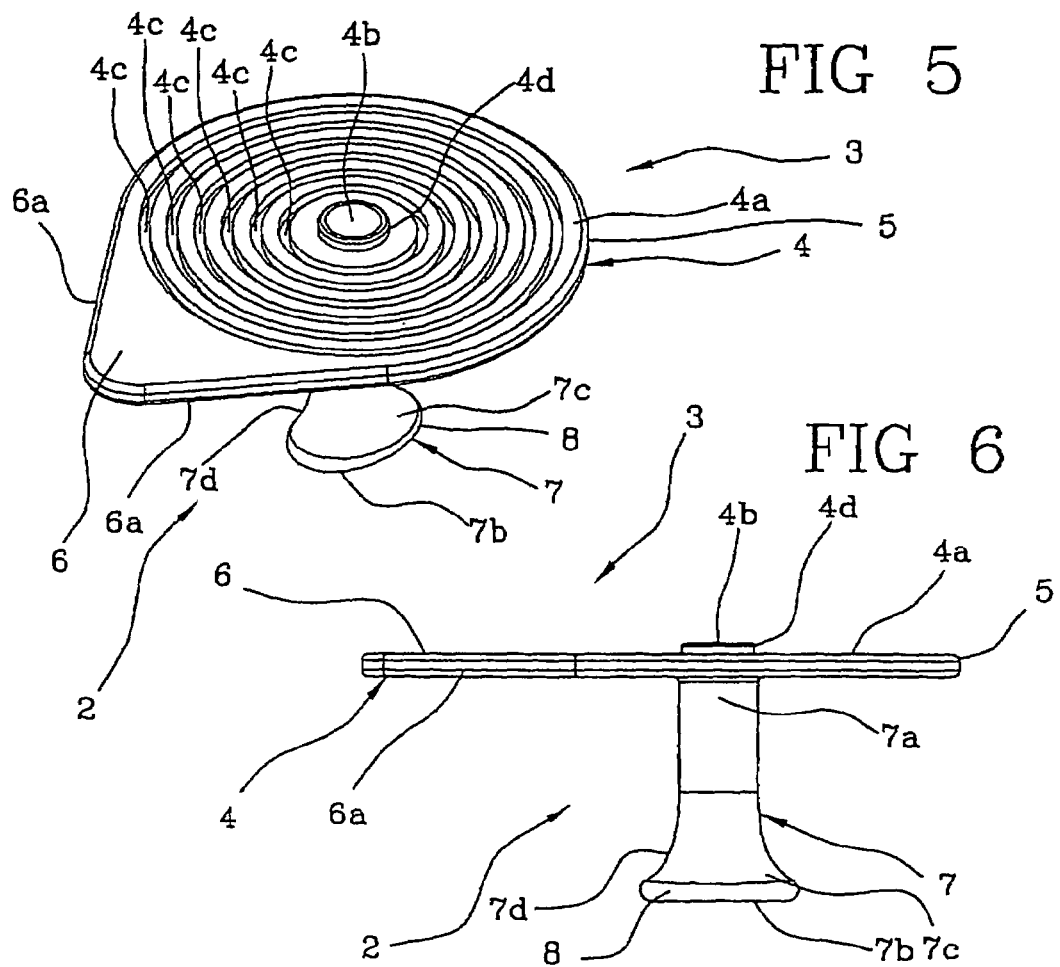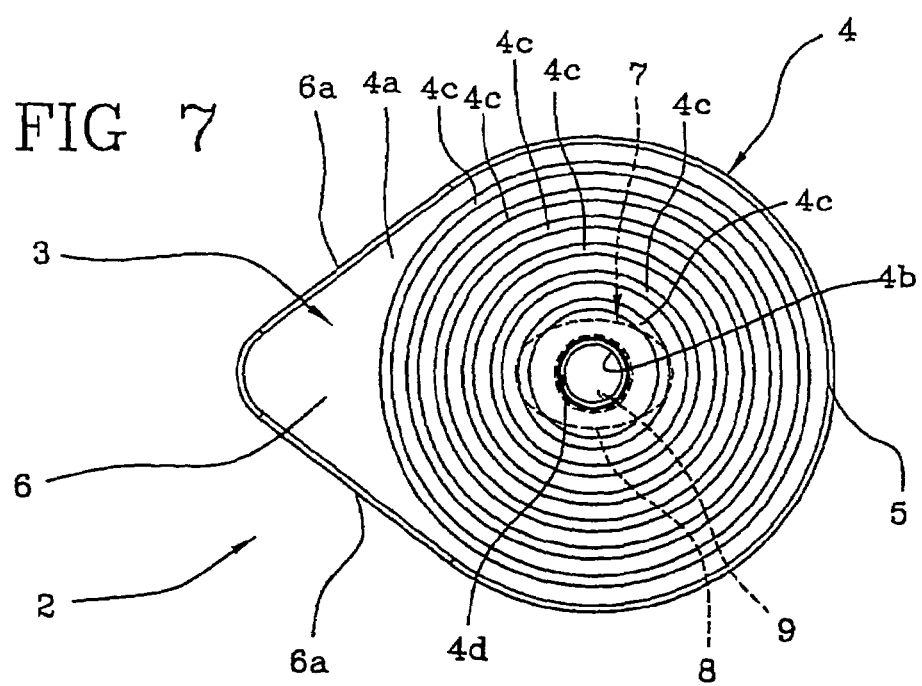

DEVICE FOR CUTTING SANITARY CONTAINERS, IN PARTICULAR SACKS, BAGS, AND/OR POUCHES FOR STOMAS

TECHNICAL FIELD

The present invention relates to device for cutting sanitary containers, in particular sacks, bags and/or pouches for stomas, comprising the characteristics set out in the preamble to claim 1.

The present invention pertains to the medical/nursing sector, and in particular it is intended to assist nurses, patients, and/or any other person, during the usual operations of preparing sanitary containers, such as sacks, bags, pouches and the like, to be applied to temporary or permanent stomas.

BACKGROUND ART

It is well known that the preparation of the aforementioned containers entails a delicate step of cutting the container itself, aimed at adapting its inlet to the peripheral dimensions of the patient's stoma. Usually, said cutting operation is performed manually by the nurse or by the patient who, after ascertaining the dimensions of the stoma, cuts, using appropriate scissors or similar cutting devices and according to his/her manual skills, the respective sanitary container.

To facilitate the adaptation of the sanitary containers to patients' stomas, some commercially available sanitary containers are provided with a series of reference guide lines to follow during the cutting operation. However, even with the aid of said reference guide lines, the precision of the cut depends exclusively on the operator's manual skills, which can be compromised by physical limitations, e.g. visual and/or tactile deficiencies.

To overcome the aforementioned problems, the Applicant has devised and patented a device for cutting sanitary containers for stomas. Said known device comprises a support structure whereon is positioned a respective sanitary container, and appropriate cutting means, able to adapt the inlet of the sanitary container to the dimensions and to the shape of the corresponding stoma of a patient. The cutting means are adapted to cut the structure of the sanitary container by means of at least a cutting blade borne by a respective supporting rod which is hinged to the structure of the device to guide the cutting blade along a closed cutting line.

To assure the adaptability of the sanitary containers to the dimensions of the respective stoma, the device further comprises a plurality of support rods with differentiated length which are replaceable in relation to the amplitude of the inlet to be obtained Although the aforementioned cutting device allows a satisfactory adjustment of the inlet of sanitary containers for stomas, the Applicant has observed that said device is not free of some drawbacks and can be improved under several aspects, mainly in relation to its ease of use, to the ease of assembly of the various components and to its structural simplicity.

In particular, the Applicant has observed that the presence of numerous support rods with different length forces the nurse to perform continual replacement of said rods, to try to obtain inlets that will precisely conform to the respective stomas, leading to a considerable time wastage and a degree of precision that is not always satisfactory.

Moreover, the known device is constituted by a high number of components that entail considerable difficulties during assembly and/or disassembly, especially if it is mounted directly by the patient or by an inexperienced nurse.

Additionally, the presence of numerous components causes high costs of production and/or marketing of the aforementioned devices which must be affordable for everyone.

DISCLOSURE OF INVENTION

The object of the present invention is to solve the problems noted in the prior art, proposing a device for cutting sanitary container, in particular sacks, bags and/or pouches for stomas, which is practical in relation to the adjustment of the amplitude of the inlet thereof, to the assembly of all components while having a simple structure which can be constructed at contained costs.

These and other objects, which shall become more readily apparent from the description that follows, are substantially achieved by a device for cutting sanitary containers, in particular sacks, bags and/or pouches for stomas, comprising the characteristics expressed in the characterising part of claim 1.

DESCRIPTION OF THE DRAWINGS

Further characteristics and advantages shall become more readily apparent from the detailed description of a preferred, but not exclusive embodiment of a device for cutting sanitary containers, in particular sacks, bags and/or pouches for stomas, in accordance with the present invention. The description shall be provided below with reference to the accompanying figures, provided purely by way of non limiting indication, in which:

FIG. 2 is an elevation view of the device of the previous figure;

FIG. 3 is a plan view of the device of the previous figure;

FIG. 5 is a perspective view of a cuffing plate and of a grip portion of the device shown in the previous figures;

FIG. 6 is an elevation view of the cutting plate and of the grip portion of the device of FIG. 5;

FIG. 7 is a plan view of the device of FIG. 5;

DESCRIPTION OF THE ILLUSTRATIVE EMBODIMENTS

Figure 1:
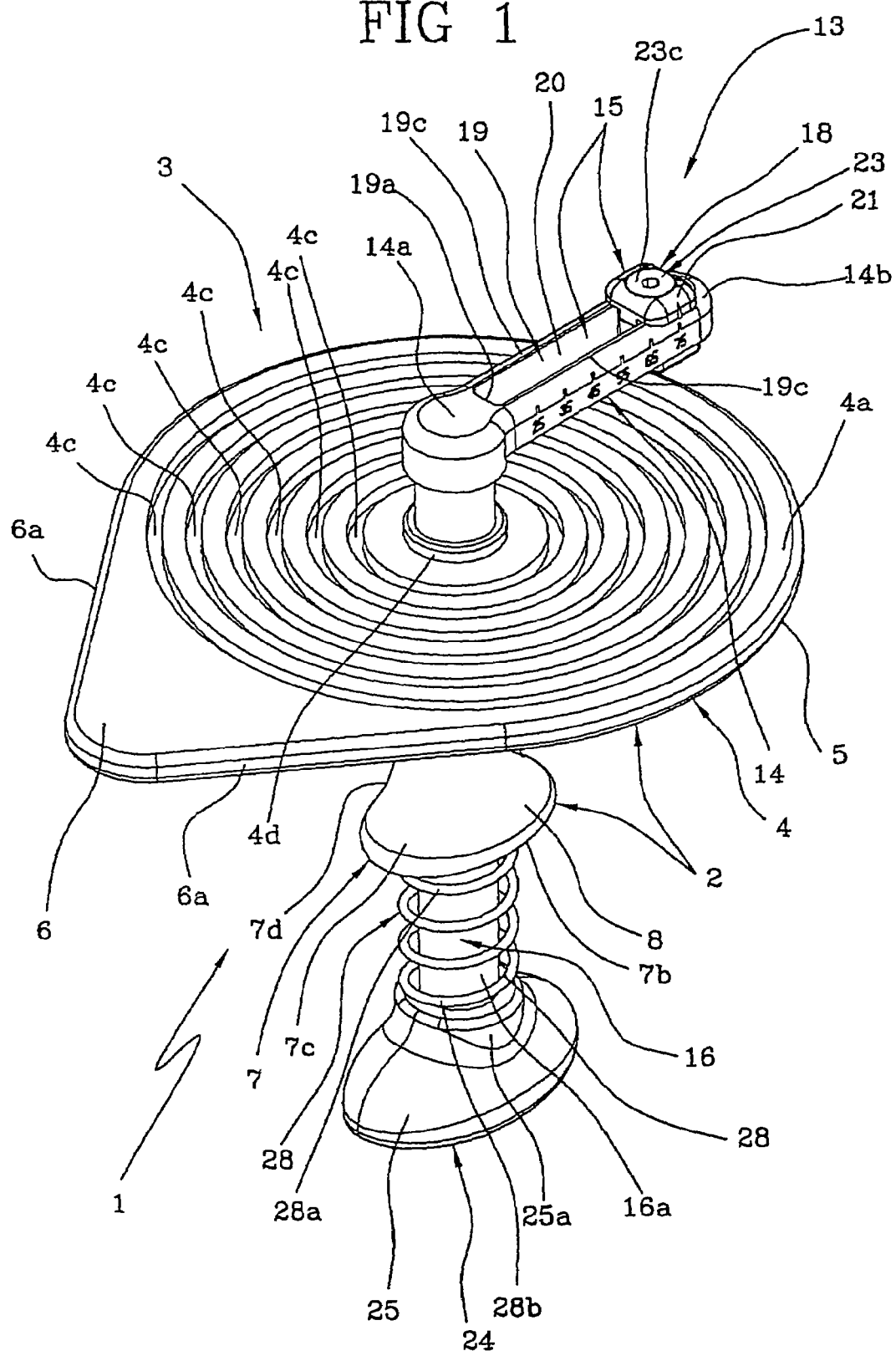
FIG. 1 is a perspective view of a device for cutting sanitary containers, in particular sacks, bags, and/or pouches for stomas, in accordance with the present invention.

With reference to the accompanying figures, the number 1 globally designated a device for cutting sanitary containers, in particular sacks, bags, and/or pouches for stomas, in accordance with the present invention.

As shown in FIGS. 1 through 4, the cutting device 1 comprises a structure 2 having at least a housing portion 3 adapted to receive in temporary engagement at least a sanitary container (not shown because it is known) for the collection of one or more fluid and/or semi-fluid bodily substances. In detail, the device 1 serves to cut sacks, bags, pouches and/or similar sanitary containers, normally used on stomas or similar openings, artificially obtained on patients who need to deviate one or more organic channels, such as intestine (enterostomas), urethra (urostomas) and others. In particular, the purpose of cutting the aforementioned containers is to adapt their inlets to the dimension, as well as to the shape, of the stomas present on the patients to protect said stomas from irritations, inflammations or other unpleasant and undesirable consequences usually due to the infiltration of extraneous substances and/or to the stagnation of organic substances. The cutting operations are conducted at the housing portion 3 of the structure 2 of the device 1 on at least a structural portion of the containers being prepared, called plate. Usually, the plate has greater rigidity than the entire structure of the container and is applied to the patient's peristomal skin by appropriate adhesive application means. The plate of each container is usually provided with a central access opening and with a plurality of graduated reference guide lines, whose purpose is to facilitate the cutting operation and the obtainment of the respective inlet.

As shown in FIGS. 1 through 7, the housing portion 3 of the structure 2, destined to receive in engagement the aforesaid sanitary containers, is defined by a bearing surface 4a of a cutting plate 4 comprised in the structure itself. In particular, the cutting plate 4 has a substantially rounded portion 5 with a substantially triangular appendage 6 defining a substantially drop-shaped contour. The rounded portion 5 extends according to a predefined circle arc, whilst the triangular appendage 6 is defined by two rectilinear edges 6a joined, at one side, to the rounded portion 5, and converging, at the other side, away from the rounded portion itself.

The cutting plate 4 further comprises a through opening 4b located substantially centrally between the rounded portion 5 and the triangular appendage 6. Around the through opening 4b of the cutting plate 4, is also provided a plurality of cutting grooves 4c extending parallel to each other according to respective closed lines each having a substantially circular development.

The structure 2 is further provided with a substantially cylindrical grip portion 7, orthogonally engaged, by means of its own attachment end 7a, to the cutting plate 4, at the opposite side relative to the bearing surface 4a thereof.

Preferably, the grip portion 7 is substantially tubular and engages the cutting plate 4 coaxially relative to the through opening 4b thereof.

As shown in FIGS. 1 and 5, and in particular in FIG. 7, the grip portion 7 of the structure 2 has, in its cross section, a substantially elliptical outer profile 8 able to favour the manual engagement of the grip portion itself, and a substantially circular inner profile 9, whose diameter is unchanged along the entire axial development of the grip portion 7 and identical to the diameter of the through opening 4b of the cutting plate 4.

Again with reference to the accompanying figures, the grip portion 7 has a free end 7b, opposite to the attachment end 7a, whereat the section of the grip portion 7 progressively grows to define a substantially cone frustum shaped portion 7c whose lateral surface 7d is slightly concave to house in engagement the heel or the fingers of a hand.

It should be noted in any case that the grip portion 7 can be obtained according to any ergonomic shape suitable for manual engagement.

Figure 8:
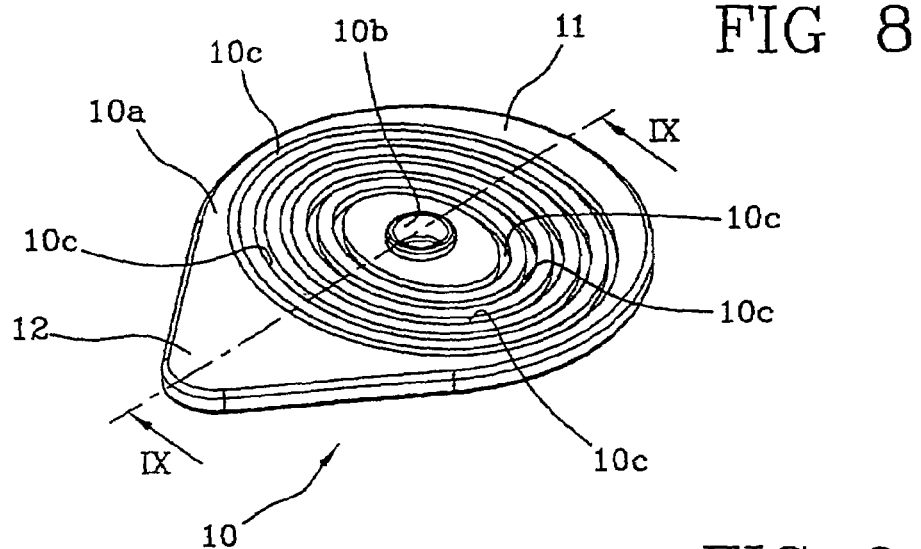
FIG. 8 is a plan view of an additional cutting plate of the device shown in the previous figures.
Figure 9:
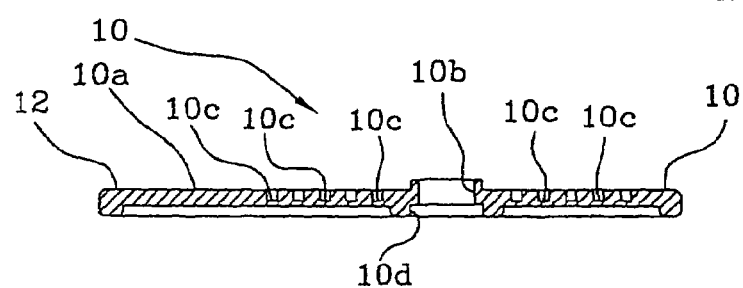
FIG. 9 is a section view of the additional cutting plate according to the trace IX-IX of FIG. 8.

As shown in FIGS. 8 and 9, the device 1 is advantageously provided with an additional cutting plate 10 preferably having a shape that is identical to the shape of the cutting plate 4 of the structure 2 of the device 1. In particular, the additional cutting plate 10 also has a substantially drop shaped contour with a rounded portion 11 and a substantially triangular portion 12. In similar fashion to the cutting plate 4, the additional cutting plate 10 has a bearing surface 10a adapted to receive in engagement at least a sanitary container and a through opening 10b located substantially centrally between the rounded portion 11 and the triangular portion 12. The additional cutting plate 10 also has a plurality of cutting grooves 10c developing at the bearing surface 10a according to respective closed development lines. Preferably, the cutting grooves 10a of the additional cutting plate 10 extend substantially parallel to each other according to a substantially elliptical development.

The additional cutting plate can be engaged on the cutting plate 4 to adapt the device 1 to elliptical cuts. More in particular, the cutting opening 10c of the additional cutting plate 10 has, at the opposite surface to its own bearing surface 10a, an invitation 10d (FIG. 9) to be fit on an insertion collar 4d projecting superiorly from the bearing surface 4a of the cutting plate 4, at the through opening 4c thereof. The additional cutting plate 10 is thus adapted to be positioned superiorly on the cutting plate 4 engaging the bearing surface 4a.

It should be observed that the solution described above, which comprises a plurality of circular cutting grooves 4c, obtained on the cutting plate 4, and a plurality of elliptical cutting grooves 10c, obtained on the additional cutting plate 10, is a design choice that in no way limits the present invention which can also comprise elliptical grooves on the cutting plate 4 and circular grooves on the additional cutting plate 10.

With reference to FIGS. 1 through 4, the aforementioned sanitary containers are cut by means of appropriate cutting means 13 operatively associated to the structure 2 of the device 1. In detail, the cutting means 13 are active at the housing portion 3 to cut a structural portion of a respective sanitary container around a predetermined reference point and according to at least a closed cutting line having identical development to at least one of the cutting grooves 4c, 10c present on the cutting plate 4, 10.

More specifically, the cutting means 13 comprise at least one support rod 14 operatively engaged to the structure 2 of the device 1 and at least a cutting element 15 operatively associated to the support rod 14. The support rod develops substantially parallel to the cutting plate 4 and engages the structure 2 of the device 1 by means of an attachment end 14a. Advantageously, the attachment end 14a of the support rod 14 rotatably engages the structure 2 at the aforementioned predetermined reference point, which is preferably located along the geometrical axis of the grip portion 7 so the support rod 14 and the cutting element 15 are free to rotate integrally about said axis.

The engagement of the attachment end 14a of the support rod 14 to the structure 2 also enables the support rod to translate along the geometric axis of the grip portion 7, between an operative position, in which the support rod 14 is located near the cutting plate 4, 10 in use and the cutting element 12 engages a respective cutting groove 4c, 10c, and a non operative position, in which the support 14 is distanced therefrom and the cutting element 15 is disengaged from the respective cutting groove 4c, 10c.

As shown in FIGS. 1 through 4, the engagement of the cutting means 15 to the structure 2 of the device 1 is assured by a substantially cylindrical actuation pivot 16 whose cross section profile is substantially circular.

Also with reference to FIGS. 1 through 4, the actuation pin 16 engages, in substantially perpendicular fashion, the attachment end 14a of the support rod 14 and is operatively engaged within the grip portion 7. In particular, the actuation pivot 16 is free to slide axially within the grip portion 7 to drive the support rod 14 and the cutting element 15 between the operative and the non operative position, and to rotate about its own longitudinal axis to guide them around the predetermined reference point.

Preferably, the actuation pivot 16 extends axially by a greater measure than the axial development of the grip portion 7 in such a way as to project therefrom both at the cutting plate 4 and of the free end 7b.

Advantageously, the actuation pivot 16 is joined to the support rod 14 to constitute therewith a single support element for the cutting element 15.

Moreover, the device 1 is advantageously provided with adjustment means 17 operatively associated to the cutting means 13 to determine the amplitude of the inlet of the sanitary container being prepared, measured along at least a predetermined direction. The adjustment means 17 comprise at least a cursor 18 operatively engaged to the support rod 14 and able to be translated along it between a position of minimum amplitude, in which the cursor 18 is positioned in proximity to the actuation pivot 16 and to the predetermined reference point, and a position of maximum amplitude, in which the cursor 18 is distanced from the actuation pivot 16 and is positioned at a free end 14b of the support 14, opposite to the attachment end 14a.

Said adjustment means 17 further comprise at least a sliding guide 19 associated to the support rod 14 to guide the cursor 18 between the positions of minimum and maximum amplitude. The sliding guide 19 is obtained directly on the support rod 14, and in particular, is defined by a through opening 20 whose contour is substantially similar to the contour of the support rod 14.

Figure 4:
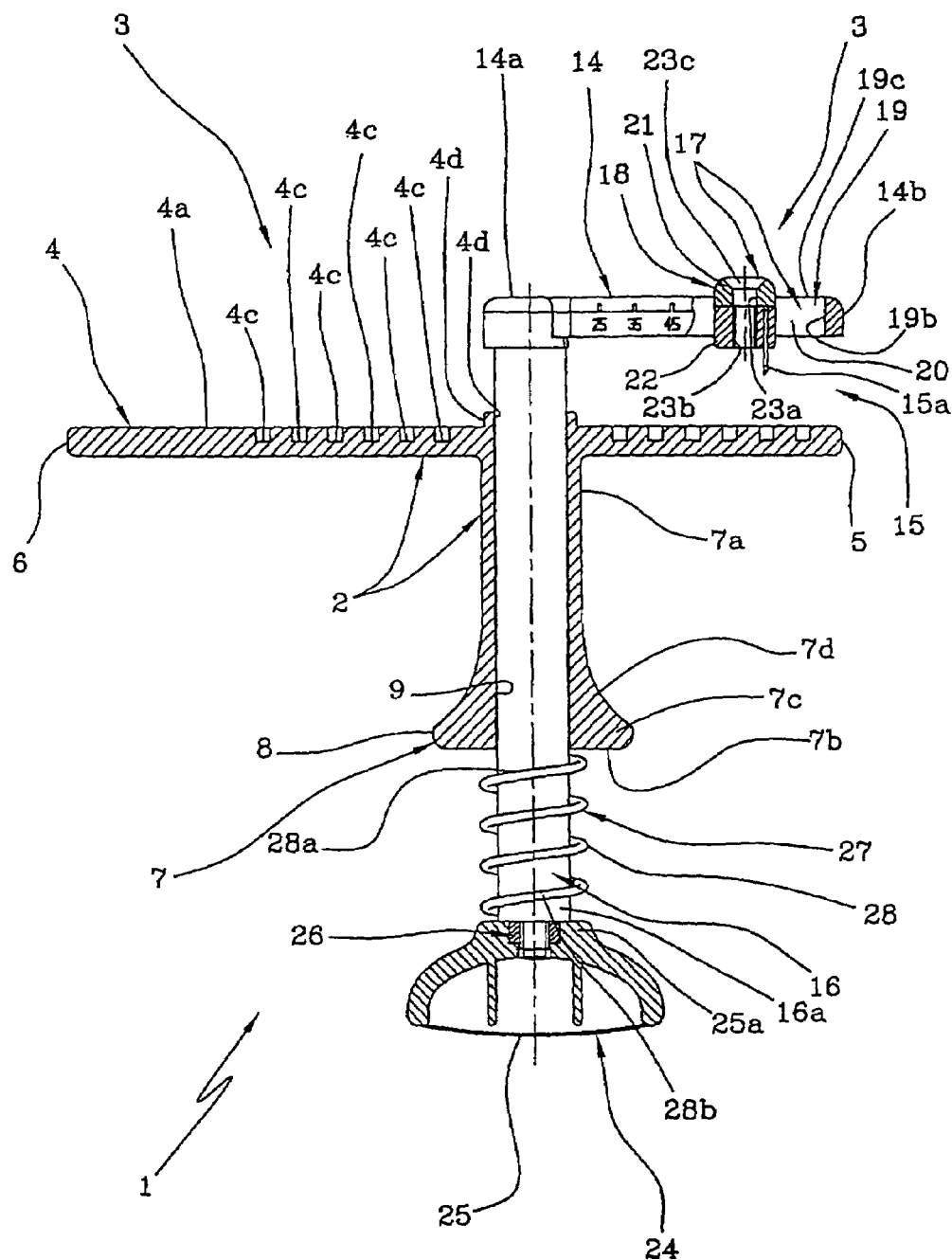
FIG. 4 is a section view of the device of the previous figures, according to the trace IV-IV of FIG. 3.

As shown in FIGS. 1, 3 and 4, the sliding guide 19 defines, on the support rod 14, a first arresting edge 19a positioned at the attachment end 14a and a second arresting edge 19b, opposite to the first one, situated at the free end 14b. The sliding guide 19 further defines a pair of sliding tracks 19c extending along the development of the support rod 14, between the first and the second arresting edge 19a, 19b, and substantially parallel relative to each other.

Figure 10:
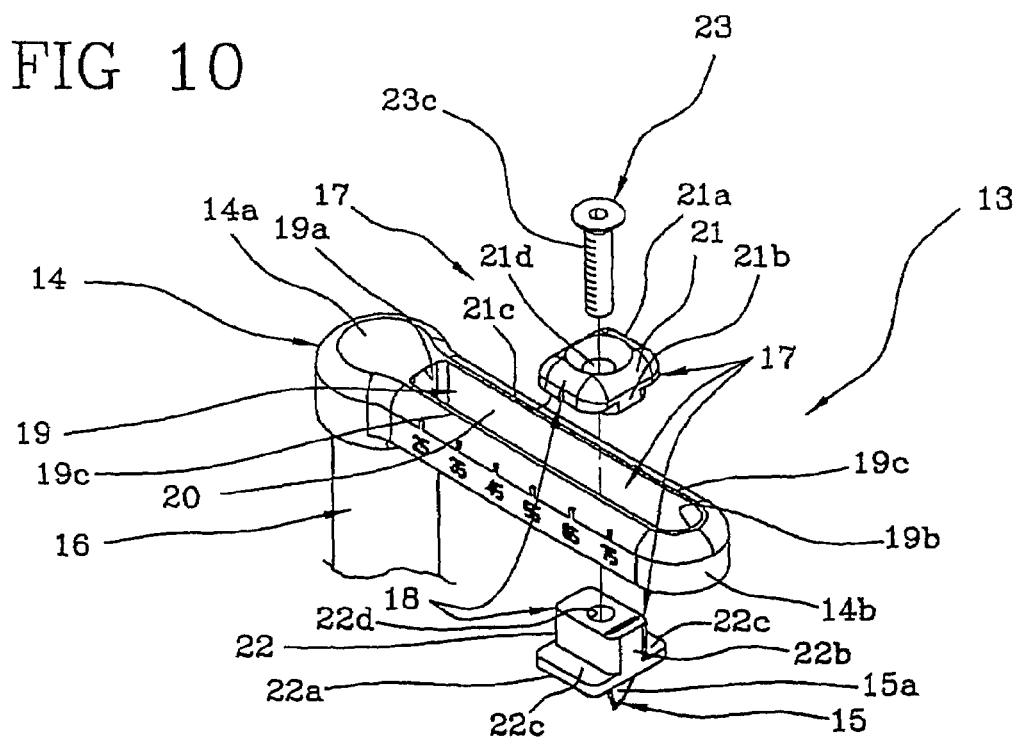
FIG. 10 is an exploded perspective view of a cursor of the device of FIGS. 1 through 4.

With reference to FIGS. 1 through 4 and to FIG. 10, the cursor 18 comprises a sliding portion 21 operatively engaged to the sliding guide 19 and a support portion 22, supporting the cutting element 15, removably engaged to the sliding portion 21 and adapted to engage the sliding guide 19. The cursor 18 is also provided connecting and locking means 23, operatively associated to the sliding and support portions 21, 22 to lock the cursor on the support rod 14 in a predetermined position.

As shown in FIG. 10, the sliding portion 21 has a substantially parallelepiped body 21a wherefrom extends centrally an engagement element 21b able to be inserted, at least partially, in the sliding seat 19. The engagement element 21b defines, on the body 21a of the sliding portion 21, a pair of sliding surfaces 21c each adapted to engage a respective sliding track 19c of the sliding guide 19. The sliding portion 21 also has at least a through opening 21d developing centrally through the body 21a and the engagement element 21b.

With reference to FIG. 10, the support portion 22 has a substantially plate-like element 22a and a substantially parallelepiped engagement element 22b extending centrally from the plate-like element 22a. The engagement element 22b defines, on the plate-like element 22a, a pair of locking surfaces 22c, each adapted to engage, at the opposite side from the sliding portion 21, the respective sliding track of the sliding guide 19. The engagement element 22b of the support portion 22 can also be inserted in the sliding guide to operate against the engagement element 22c of the sliding portion 22.

Additionally, as shown in FIG. 10, the support portion 22 has a through opening 22d, extending, substantially centrally, from the plate-like element 22a to the engagement element 22b and able to be aligned to the through opening 21d of the sliding portion 21.

As shown in FIG. 4, the connecting and locking means 23 comprise a first thread 23a obtained in the through opening 21d of the sliding portion 21 and a second thread 23b obtained in the through opening 22d of the support portion 22. The connecting and locking means 23 further comprise a threaded locking element 23c able to be inserted by screwing into the through openings 21d, 22d of the sliding and support portions 21, 22. In detail, the threaded locking element 23 operates between a locking condition, in which the sliding and support portions 21, 22 are pressed against each other and the sliding and locking portions 21c, 22c are pressed against the sliding tracks 19c of the sliding guide 19, and a sliding condition, in which the sliding and locking portions 21, 22 are not pressed against each other and the locking surfaces 22c are disengaged from the sliding tracks 19c. In the locking condition, the sliding and support portions 21, 22 collaborate to maintain the cursor securely engaged to the support rod 14 without freedom of motion, whilst in the sliding condition the threaded locking element 23c is loosened to allow the cursor 18 to slide on the support rod 14 between the position of minimum and maximum amplitude.

Still with reference to FIGS. 4 and 10, the cutting element 15 is integrated to the support portion 22 of the cursor 18 and extends through the plate-like element 22a and the engagement element 22b according to a side by side position relative to the through opening 22d. Preferably, the cutting element 15 has a substantially laminar cutting portion 15a, for cutting the sanitary container to be prepared.

As shown in FIGS. 1 through 4, the device 1 comprises manual command means to actuate the support rod 14 and the cutting element 15 between the operative and non operative positions and around the predetermined reference point. In detail, the command means 24 comprise at least an operating knob 25, preferably egg-shaped, removably engaged on the actuation pivot 16 at the opposite side from the cutting plate 4. Preferably, the operating knob 25 is screwed on the actuating pivot 16 by means of a threaded coupling 26, partly defined on a free lower end 16a of the actuation pivot 16, and partly on an upper portion 25a of the operating knob itself.

The device further comprises elastic thrust means 27 operatively associated to the cutting means 13 to move the support rod 14 and the cutting element 15 from the non operative position to the operative position. In particular, the elastic thrust means 2 are operatively interposed between the grip portion 7 and the operating knob 25 are constituted by at least one helical spring 28 fitted on the actuation pivot 16. The helical spring 28 has a first end 28a engaged against the grip portion 7 and a second end 28b, opposite to the first, engaged against the operating knob 25. In the absence of interventions by the nurse or by the patient, the helical spring 28 tends to maintain the actuation pivot 16 lowered with the support rod 14 and the cutting element 15 positioned in the operative position. This takes place because of the thrust which said spring 28 exerts on the operating knob 25 in the opposite direction to the grip portion 7.

The operation of the cutting device 1, described above in prevalently structural sense, is as follows.

After ascertaining the dimensions and the shape of the stoma whereon the respective sanitary container is to be applied, the nurse or the patient decides whether to use the device 1 with the cutting plate 4 destined to circular cuts or prepare thereon the additional cutting plate 10 destined to elliptical cuts. Once the device 1 is prepared, the operating knob 25 is thrust manually towards the grip portion 7 compressing the helical spring 28. The actuation pivot 16 is then raised bring the support rod 14 and the cutting element 15 in the non operative position. Maintaining the cutting element 15 and the support rod 14 in the non operative position, the cursor 18 is positioned along the support rod 14 in a suitable position to execute the inlet according to the measurements of the respective stoma. If the inlet to be obtained is circular, the cursor 18 is fastened to the support rod 14 intervening directly on the threaded element 23c. In this case, the threaded locking element 23c is manually operated from the sliding condition to the locking condition to press the sliding and support portions 21, 22, against each other and against the sliding tracks 19c of the sliding guide 19.

If instead the inlet must be elliptical, the cursor 18 is not locked on the support rod 14 thereby being free to slide over it.

Subsequently, the sanitary container is positioned on the bearing surface 4a, 10a. To ensure a correct positioning of the container on the structure 2 of the device 1, the support rod 14 with the cursor 18 and the cutting element 15 is inserted into the opening present on the plate of the container itself.

The operating knob 25 is then released to allow the helical spring 28 to bring it back to the original position. The actuation pivot 26 is then lowered and the support rod 14 with the cutting element is brought from the non operative position to the operative position. When the support rod reaches the operative position, the cutting portion 15a of the cutting element 15 lacerates the plate of the container from the interior to the exterior, engaging a respective cutting groove 4c, 10c of the cutting plate 4, 10.

The operating knob 25 is then rotated about the geometric axis of the grip portion 7, according to an angle of 360°, to drive in rotation the actuation pivot 16. Consequently, both the support rod 14 and the cutting element 15 rotate integrally with the rotation pivot 16 about the aforementioned axis. During its own rotation, the cutting element 15 cuts the lacerated container along the entire development of the respective cutting groove.

If the cut is elliptical, the cursor 18 is not locked in order for it to be free to slide on the support rod 14 on the action of the cutting groove 10c of the additional cutting plate 10 previously mounted on the circular cutting plate 4 it is moved along it by means of the respective elliptical cutting groove 10c. More in detail, the elliptical cutting groove 10c guides the cutting element 15 according to an elliptical trajectory determining a rectilinear alternating displacement of the cursor 18 on the support rod 14.

Once the cut is complete, the operating knob 15 is again thrust towards the grip portion 7 to enable to extract the prepared container from the support rod 14, disengaging the container from the cutting plate 4, 10 of the device 1.

The present invention solves the problems encountered in the prior art and achieves the proposed objects.

First of all, the cutting device according to the present invention allows to obtain, on sanitary containers for stomas, inlets that precisely conform to patients' stomas.

It should also be noted that the device described and claimed herein allows to adjust the shape and dimensions of the inlet of the container in easy and practical fashion. In particular, the presence of the cursor 18, bearing the cutting element 15, slidably engaged to the support rod 14 allows the immediate adjustment of the amplitude of the inlet to be obtained on the containers being prepared in the absence of any replacements of containers and parts of the device itself.

Additionally, it should also be noted that the device described above can easily be assembled and/or disassembled both by a patient and by inexperienced nurses. This characteristic is determined by a small number of components and by structurally simple connections. As is readily apparent, the support rod 14 is constructed in a single piece with the actuation pivot 16 to form a single actuation and support element for the cutting element and the cutting plate 4 is constructed in a single piece with the grip portion 7 to form a single support and cutting structure of the device 1.

A simple structure constituted by a few components allows a considerable reduction in construction and marketing costs.

The invention claimed is:

1. A device for cutting sanitary containers, in particular sacks, bags, and/or pouches for stomas, said device comprising a structure having at least a housing portion, having a cutting plate, adapted to receive in engagement at least a sanitary collection container to be cut, cutting means operatively associated to said structure and active at said housing portion to cut at least a structural portion of said sanitary container about a predetermined reference point and according to a closed cutting line, adjustment means operatively associated to said cutting means to determine the amplitude of the structural portion to be removed from said sanitary container along at least a predetermined direction, at least an additional cutting plate able to be associated to said cutting plate by means of an engagement of a bearing surface thereof, said additional cutting plate having a bearing surface defining said housing portion of said structure.

2. A device as claimed in claim 1, wherein said structure comprises: a substantially cylindrical grip portion; said cutting plate engaging to one end of said grip portion, said cutting plate extending prevalently on a plane that is substantially perpendicular to an axial development of said grip portion.

3. A device as claimed in claim 2, wherein said cutting plate is provided with a bearing surface facing said cutting means and having at least a through opening that is coaxial relative to the grip portion, said bearing surface of said cutting plate defining said housing portion of said structure.

4. A device as claimed in claim 3, wherein said bearing surface is provided with a plurality of cutting grooves co-operating with said cutting means to assure the cutting of the structural portion of said sanitary container, each cutting groove developing around the predetermined reference point substantially parallel relative to each other and according to a substantially circular development line.

5. A device as claimed in claim 2, wherein said cutting plate and said grip portion are joined in a single piece.

6. A device as claimed in claim 1, wherein said bearing surface of said additional cutting plate is provided with a plurality of cutting grooves co-operating with said cutting means to assure the cutting of the structural portion of said sanitary container, each cutting groove developing around the predetermined reference point substantially parallel to each other and according to a substantially elliptical development line.

7. A device for cutting sanitary containers, in particular sacks, bags, and/or pouches for stomas, said device comprising a structure having at least a housing portion, having a cutting plate, adapted to receive in engagement at least a sanitary collection container to be cut, cutting means operatively associated to said structure and active at said housing portion to cut at least a structural portion of said sanitary container about a predetermined reference point and according to a closed cutting line, adjustment means operatively associated to said cutting means to determine the amplitude of the structural portion to be removed from said sanitary container along at least a predetermined direction, said cutting means comprising at least a support rod operatively engaged to said structure, developing substantially parallel relative to said cutting plate and being movable between an operative position, in which it is situated near said cutting plate, and a non-operative position, in which it is distanced from said cutting plate, the device further comprising at least a cutting element operatively associated to said support rod, said cutting element engaging a respective cutting groove of said cutting plate when the support rod is situated in the operative position, and disengaging said cutting plate when the support rod is in non-operative position, the device further comprising elastic thrust means operatively associated to said cutting means to move said support rod and said cutting element from the non-operative position to the operative position.

8. A device as claimed in claim 7, wherein said support rod rotatably engages the structure by means of an attachment end fastened to said cutting plate, at the predetermined reference point, which is located along the geometric axis of said grip portion so that said support rod and said cutting element are free to rotate integrally around said axis and the reference point itself.

9. A device as claimed in claim 7, wherein said cutting means further comprise a substantially cylindrical actuation pivot, rotatably engaged in the grip portion and free to slide axially along said portion to drive the support rod integrally with said cutting element between the operative position and the non operative position, said actuation pivot rigidly engaging the attachment end of said support rod and extending according to a greater measure than the axial development of said grip portion so it projects therefrom both at said cutting plate and at the opposite side therefrom.

10. A device as claimed in claim 9, wherein said actuation pivot and said support rod are orthogonally joined in a single piece to constitute a single support element for the cutting element.

11. A device as claimed in claim 7, wherein said means for adjusting said cutting means comprise at least one cursor operatively engaged to said support rod, said cursor being translatable along said support rod between a position of minimum amplitude in which the cursor is positioned near the predetermined reference point, and a position of maximum amplitude, in which the cursor is positioned distant from the predetermined reference point in correspondence with a free end of said support rod, opposite to the attachment end.

12. A device as claimed in claim 11, wherein said adjustment means further comprise a sliding guide to guide said cursor between the positions of minimum and maximum amplitude, said sliding guide being associated to said support rod of said cutting means.

13. A device as claimed in claim 12, wherein said sliding guide is obtained directly on the structure of said support rod and is defined by a through opening having a contour that is substantially similar to the contour of said support rod, said through opening defining, on said support rod, a first arresting edge, positioned in correspondence with said actuation pivot, a pair of sliding tracks extending parallel to each other along the development of said support rod and a second arresting edge, opposite the first, and positioned in correspondence with the free end of said support rod.

14. A device as claimed in claim 12, wherein said cursor comprises: a sliding portion operatively engaged to said sliding guide to assure the ability of said cursor to slide between the positions of minimum and maximum amplitude, a portion for supporting said cutting element, removably engaged to said sliding portion; connecting and locking means operatively associated to said sliding and support portions to lock said cursor on said sliding guide in a predetermined position.

15. A device as claimed in claim 14, wherein said sliding portion has: a substantially parallelepiped body wherefrom extends an engagement element able to be inserted into the through opening of said support rod defining said sliding guide, said engagement element defining, on the body of said sliding portion, a pair of sliding surfaces each adapted to engage a respective sliding track of said sliding guide; at least a through opening developing through the body of said sliding portion in correspondence with said engagement element.

16. A device as claimed in claim 14, wherein said support portion has: a substantially plate-like element; a substantially parallelepiped engagement element extending centrally from said plate-like element and defining thereon at least a pair of locking surfaces each adapted to engage a respective sliding track of said sliding guide, at the opposite side relative to the sliding portion, said engagement element of said support portion being able to be inserted into the through opening of said support rod, defining said sliding guide, and engaging the engagement element of said sliding portion; at least a through opening extending between the plate-like element and the engagement element.

17. A device as claimed in claim 16, wherein said cutting element is integrated in the support portion of said cursor through said plate-like element and said engagement element, said cutting element being positioned side by side with respect to the through opening of said support portion.

* * * * *